United States Patent [19]
Yamashita et al.

[11] Patent Number: 5,505,827
[45] Date of Patent: Apr. 9, 1996

[54] METHOD OF DETECTING CARBIDES IN ALLOY STEELS BY ELECTROCHEMICAL POLARIZATION

[75] Inventors: Mitsuo Yamashita, Kawasaki; Nobuo Kato, Sendai; Naokatsu Sakuma, Sendai; Terutsugu Watanabe, Sendai, all of Japan

[73] Assignees: Fuji Electric Co., Ltd., Kanagawa; Tohoku Electric Power Co., Inc., Miyagi, Japan

[21] Appl. No.: 155,873

[22] Filed: Nov. 23, 1993

Related U.S. Application Data

[63] Continuation of Ser. No. 110,005, Aug. 23, 1993, abandoned.

[30] Foreign Application Priority Data

Feb. 24, 1993  [JP]  Japan ..................... 5-059607

[51] Int. Cl.$^6$ ................................. G01N 27/26
[52] U.S. Cl. ............... 205/791.5; 204/400; 204/404; 204/412; 204/434; 205/775.5
[58] Field of Search ............ 204/153.1, 153.11, 204/434, 404, 400

[56] References Cited

U.S. PATENT DOCUMENTS

| | | | |
|---|---|---|---|
| 3,479,256 | 11/1969 | Smith et al. ............... | 204/153.11 |
| 3,925,168 | 12/1975 | Costas ........................ | 204/434 |
| 3,943,043 | 3/1976 | Billington .................. | 204/434 |
| 4,160,702 | 7/1979 | Baxter ........................ | 204/434 |

OTHER PUBLICATIONS

"Evaluation of the Degraded CrMoV Steel by Electrical Polarization Method", Mitsuo Yamashita et al., Proceedings of the 1992 Annual Meeting of JSME/MMD, No. 920–72, pp. 437–438, Sep. 2–3, 1992.

*Primary Examiner*—T. Tung
*Attorney, Agent, or Firm*—Finnegan, Henderson, Farabow, Garrett & Dunner

[57] ABSTRACT

An electrolyte such as a saturated picric acid solution in a cell for measuring electrochemical polarization is placed in contact with an alloy steel such as a CrMoV steel which has been subjected to a high-temperature and stress-applied condition, and a potential is swept between the CrMoV steel and a salt bridge in the cell, whereby the Mo-rich carbide $M_6C$ undergoes a dissolution reaction at a potential near a specified value and this reaction is visible as the secondary anode peak current, or the second appearance of peak current on the waveform of electric polarization. Since the secondary anode peak current is closely related to the amount of $M_6C$ precipitation, the progress of degradation in the CrMoV steel can be evaluated by a simple method with good precision.

8 Claims, 7 Drawing Sheets

L: LOW TEMPERATURE SECTION
M: MODERATE TEMPERATURE SECTION
MD: MODERATE TEMPERATURE SECTION AFTER DEBRITTLEMENT
H: HIGH TEMPERATURE SECTION
HD: HIGH TEMPERATURE SECTION AFTER DEBRITTLEMENT

METHOD OF DETECTING CARBIDES IN ALLOY STEELS BY ELECTROCHEMICAL POLARIZATION

This application is a Continuation of U.S. patent application Ser. No. 08/110,005, filed Aug. 23, 1993 under 37 C.F.R. 1.53, now abandoned.

BACKGROUND OF THE INVENTION

The present invention relates to a method of detecting carbides in alloy steels that are related to creep damage which occurs in a hot and stress-loaded state.

More than 70% of the steam turbines currently in operation have been in service for periods longer than 10 years. Since the parts of those turbines are used at elevated temperatures, the development of a reliable diagnostic technique for predicting the remaining life of turbine parts by measuring the degree of material degradation in a nondestructive manner is important.

The CrMoV steel used as the structural material of steam turbines is subject to various types of damage, including "creep damage" that occurs if stress is loaded under the high-temperature condition, "fatigue damage" that results from repeated force, and "temper damage" that is characteristic of the CrMoV steel.

Of these damages, the "creep damage" requires the most serious consideration. The CrMoV steel is provided with high strength by dispersing fine carbides and dislocation structures in the metal matrix. However, as the steel is used at high temperatures for a long-term period, material degradation will occur on account of such factors as the precipitation and coarsening of carbides and the recovery of dislocation structures and it is accelerated by the action of a stress load. Furthermore, voids will develop at grain boundaries and connect one another until a crack occurs. Two methods are used today as nondestructive techniques for measuring the creep damage: they are i) evaluation by the degree of softening in the material hardness (which is hereunder referred to as a "hardness method") and ii) evaluation by the amount of creep voids that develop at grain boundaries (which is hereunder referred to as a "creep void method").

The conventional "hardness" method and "creep void" method have had the following problems. With the hardness method, the initial hardness of the specimen in the virgin state is used as the reference for evaluating the degree of degradation in the specimen in terms of either the amount of hardness drop that occurred as a result of long-term service or the ratio of hardness drop (the measured value divided by the initial value). It is therefore necessary for the success of the hardness drop method to predetermine the initial value of the hardness of the specimen and, if the initial value is unknown, precise estimation of the initial value is critically important. In most cases, the value of hardness of an undamaged area (e.g., the coupling portion of a steam turbine's rotor which is used at low temperatures) is substituted as the initial value but in the case of a structural member having a distribution in the values of hardness (which hence are not uniform), the initial value of the hardness of the area to be evaluated cannot be estimated with high precision.

The creep void method has the inherent problem that the conditions for the formation of voids and the measurement values are subject to variations and, hence, the method is suitable for evaluating the degree of degradation in specimens that are in the second half of the progress of creep damage (>40 to 50%), with 100% creep damage corresponding to the occurrence of creep rupture. However, in view of the fact that most of the machines in current service that need be evaluated for remaining life are found to have experienced approximately less than 40% creep damage on the basis of theoretical estimation, one may well say that the creep void method does not guarantee satisfactory precision in evaluation. A further problem with the creep void method is its low operational efficiency since the microscopic metallurgical structure of the specimen's surface need be transferred to a replica film, which is then subjected to a measurement in laboratory using a suitable instrument such as a scanning electron microscope.

SUMMARY OF THE INVENTION

The present invention has been accomplished under these circumstances and has an object to provide a method of detecting carbides in alloy steels by electrochemical polarization, which method can be applied to actual models of machines and which yet is capable of evaluating the degree of degradation in the machine part of interest with high efficiency and precision.

The above-stated object of the present invention can be attained by a method that comprises placing a specimen of alloy steel in contact with an electrolyte, or a saturated picric acid solution, in a cell for the measurement of electrochemical polarization, sweeping a potential between the specimen and the salt bridge in the cell to produce an electric polarization waveform, and detecting the precipitation of a Mo-rich carbide $M_6C$ in the specimen and the amount thereof on the basis of the empirical fact that the second peak appearance of anode current in the polarization waveform is closely related to the precipitation of $M_6C$.

If a potential is swept between the specimen and the salt bridge in a polarization measuring cell that contains a saturated picric acid solution in contact with the specimen, an electrochemical reaction that is influenced by the metallurgical structure at the surface of the specimen produces changes in the anode current between the specimen and a counter electrode as a function of the swept potential, namely, a polarization waveform representing the relationship between the potential and the anode current is produced. If the alloy steel is a CrMoV steel, a reaction for the dissolution of a Mo-rich carbide $M_6C$ occurs near a specified potential value and this reaction is visible as the secondary anode peak current, or the second appearance of peak current on the waveform of electric polarization. Since the secondary anode peak current is closely related to the amount of $M_6C$ precipitates, it can be used as an index for the estimation of the degree of degradation in the CrMoV steel that occurs when a stress is applied under a high-temperature condition.

DETAILED DESCRIPTION OF THE INVENTION

The present invention will be described in greater detail with reference to a working example, in which a rotor of a steam turbine that had been put to prolonged actual service was subjected to tests. Stated more specifically, specimens were taken from the rotor that had been run for $14 \times 10^4$ h and which had been used at temperatures of 60° C. (in the low-temperature section), 440° C. (in the moderate-temperature section), and 538° C. (in the high-temperature section). For the moderate- and high-temperature sections, additional specimens were prepared by performing debrittlement at 650° C.×1 h.

The rotor was made of a low-alloy CrMoV steel having the components shown in Table 1 below.

TABLE 1

| Element | Content, % |
|---------|------------|
| C  | 0.21  |
| Si | 0.33  |
| Mn | 0.74  |
| P  | 0.006 |
| S  | 0.005 |
| Ni | 0.60  |
| Cr | 1.21  |
| Mo | 1.08  |
| V  | 0.28  |
| As | 0.020 |
| Sn | 0.017 |
| Sb | 0.005 |

Figure 1A:
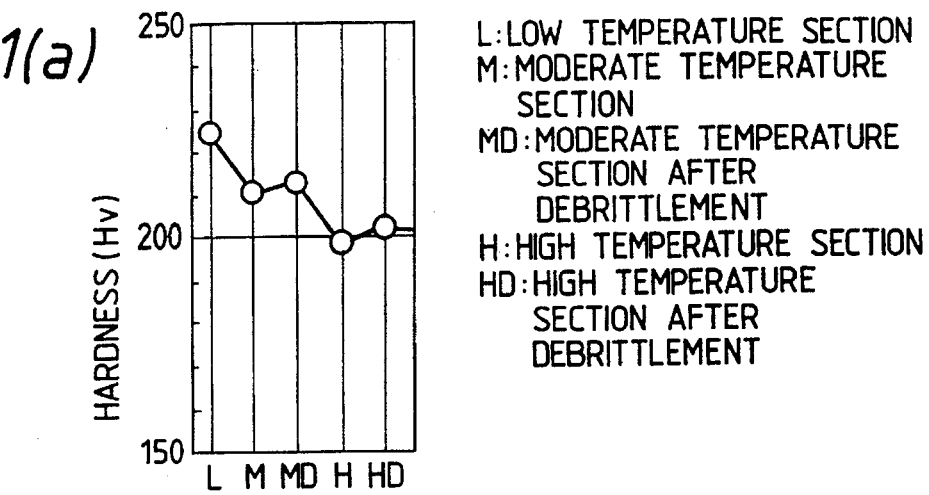
FIGS. 1(a), 1(b) and 1(c) are a set of diagrams showing the characteristic of each specimen as tested by the method of the present invention, FIG. 1(a) plotting the hardness of the specimens, FIG. 1(b) plotting the size of carbides, and FIG. 1(c) plotting the fracture appearance transition temperature (FATT) in a Charpy impact test.
Figure 1B:
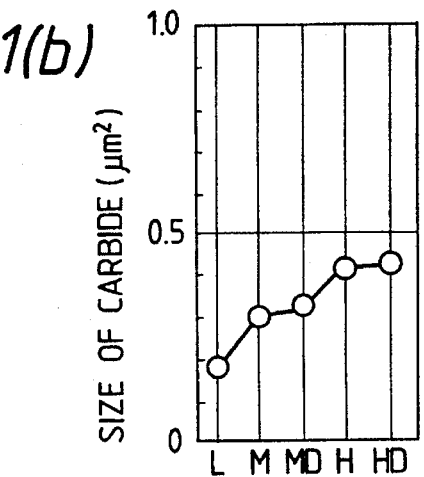
Figure 1C:
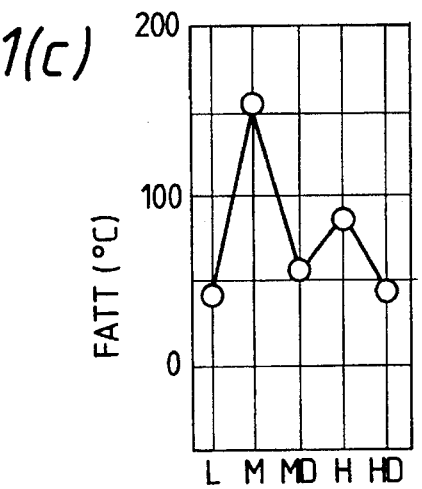

FIGS. 1(a) to 1(c) show graphically the basic material characteristics of the specimens; FIG. 1(a) shows the hardness of the specimens; FIG. 1(b) shows the size of carbides in the specimens; and FIG. 1(c) shows the fracture 67 appearance transition temperature (FATT) data obtained by a Charpy impact test. In each of FIGS. 1(a) to 1(c), L denotes a specimen of the low-temperature section, M a specimen of the moderate-temperature section, MD a specimen after debrittlement of the moderate-temperature section, H a specimen of the high-temperature section, and HD a specimen after debrittlement of the high-temperature section.

As FIG. 1(a) shows, the hardness of the specimens decreased with the increasing use temperature and, as FIG. 1(b) shows, the size of carbide increased with the increasing use temperature, whereupon material degradation occurred. The precipitation of carbides is accompanied by the diffusion of C and other elements and accelerates the recovery of dislocations in the surrounding areas, thereby inducing the drop in specimen's hardness. Hence, the size of carbides is closely related to the drop in hardness. On the other hand, as FIG. 1(c) shows, the value of FATT which is indicative of the degree of embrittlement increased markedly in the specimens of the moderate-temperature section which were in the temperature range for the high likelihood of embrittlement in the steel species under consideration. Upon debrittlement, the FATT level of those specimens was recovered to that of the specimens of the low-temperature section which were inherently low in material degradation. It is known that the embrittlement of the CrMoV steel originates from the segregation of impurities such as P at grain boundaries during service under elevated temperatures and the recovery of FATT upon debrittlement demonstrates clearly that impurities are sufficiently diffused to the initial state.

Figure 2:
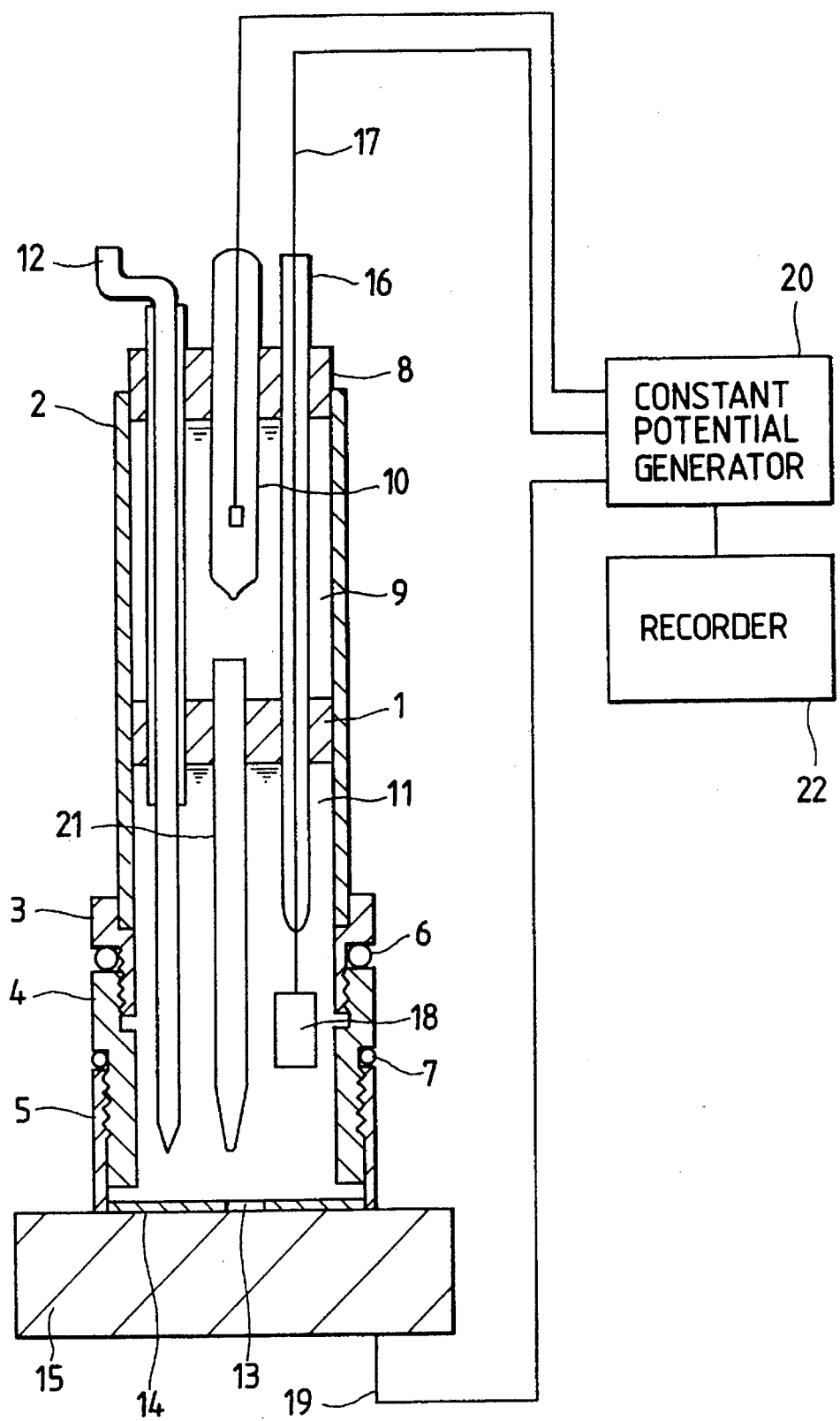
FIG. 2 is a schematic cross-sectional view showing the construction of the cell used in the method of the present invention to measure electric polarization.

FIG. 2 is a schematic cross-sectional view showing the construction of the cell used in the example under consideration for measuring electric polarization. As shown, the cell is roughly divided into two parts, the upper reference electrode portion and the lower polarization measuring electrolyte portion, by an acrylic resin plate 1. The cell container is also made of an acrylic resin throughout and the electrolyte portion consists of four containers 2 to 5 that are splittable to permit easy installation of the inside parts; the four containers are secured together by either bonding or a thread mechanism and held in close contact by means of rubber rings 6 and 7. The top opening of the first container 2 is closed with a rubber stopper 8 and the reference electrode portion is filled with a saturated KCl solution and also fitted with a reference electrode 10 that is inserted through the rubber stopper 8 from above so that it is located substantially in the center of the cell. The electrolyte portion is injected with an electrolyte 11 (saturated picric acid solution) via a glass tube 12 that penetrates the rubber stopper 8 and the acrylic resin plate 1. In the example under consideration, the temperature of the electrolyte 11 is held at 25° C. by a temperature raising and holding means (not shown). The bottom of the cell is closed with a rubber plate 14 having a through-hole 13 in the center and a specimen to be measured 15 is set up in contact with the surface of the rubber plate 14 that is opposite the side in contact with the electrolyte 11. Hence, the electrolyte 11 makes direct contact with part of the surface of the specimen. A platinum (Pt) counter electrode 18 is attached to one end of a conductor 17 that is guided through a glass tube 16 to become exposed into the electrolyte 11. The glass tube 16 penetrates the rubber stopper 8 and the acrylic resin plate 1. The other end of the conductor 17 is connected to a constant potential generator 20, to which a conductor 19 from the specimen 15 is also connected. The constant potential generator 20 generates a potential that is applied between the specimen 15 and a salt bridge 21. Upon application of the potential, an electrochemical reaction occurs at the surface of the specimen 15 and an anode current starts to flow between the counter electrode 18 in the cell and the specimen 15. The amount of the anode current is measured with the constant potential generator 20 via the reference electrode 10 which is also connected to the generator 20.

Figure 3:
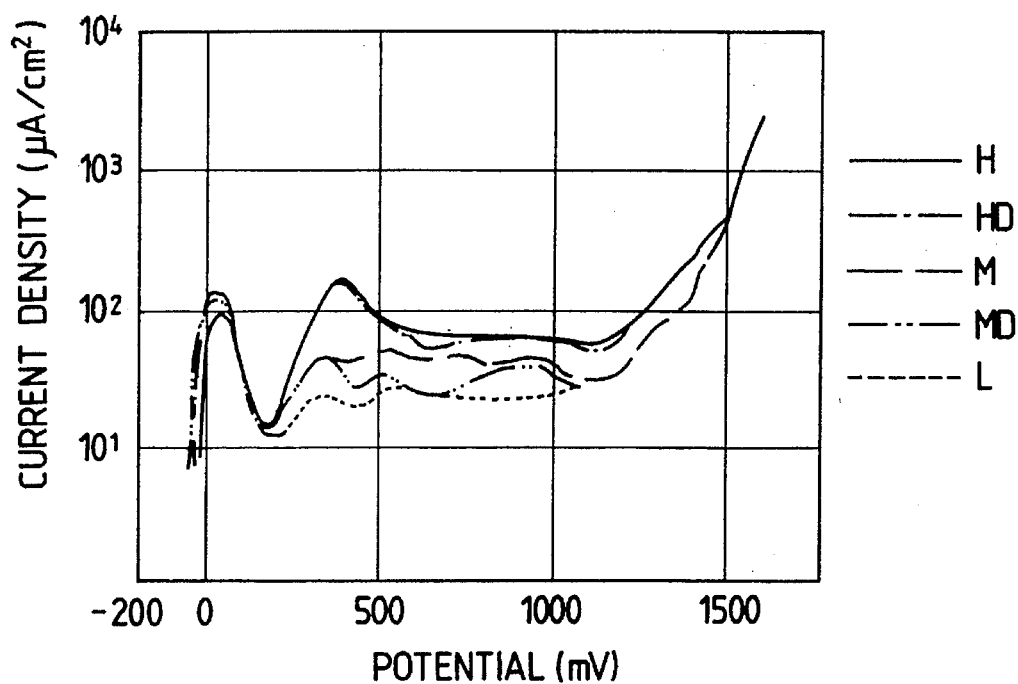
FIG. 3 is a diagram showing the waveform electric polarization as measured with the cell shown in FIG. 2.

The anode current flowing between the counter electrode 18 and the specimen 15 will vary with the properties of the surface of the specimen 15 and the electrochemical reaction occurring at its surface. The potential was swept from the initial value to 1,500 mV on the specimens having the chemical compositions shown in Table 1 and the resulting waveforms of electric polarization were read on a recorder 22 which produced outputs as shown in FIG. 3. The graph of FIG. 3 shows the relationship between the swept potential and the density of anode current produced. The curves in FIG. 3 are identified by the same abbreviations (L, M, MD, H and HD) as used in FIGS. 1(a), 1(b), and 1(c) to denote the individual specimens.

Figure 4:
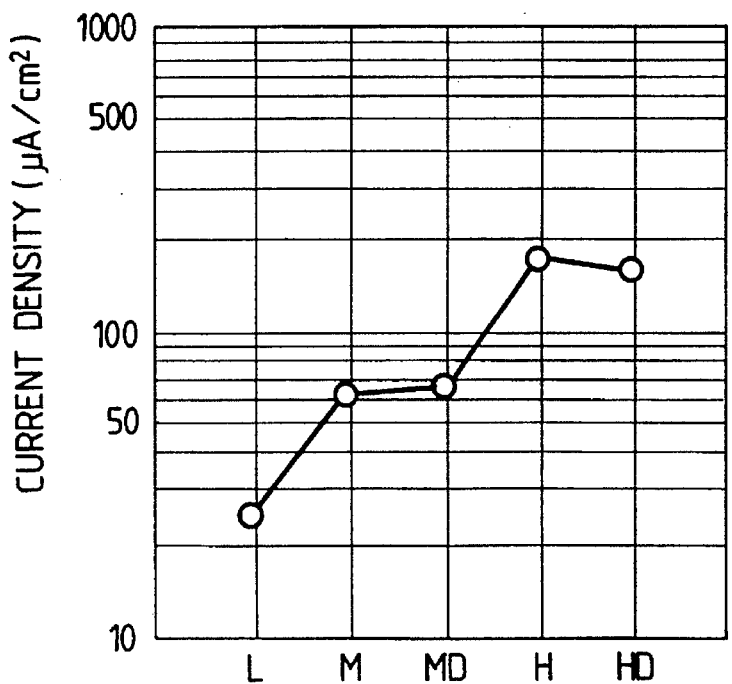
FIG. 4 is a graph plotting the secondary anode peak current on the waveform of electric polarization against the material of specimens.

FIG. 4 is a graph plotting for each specimen type the secondary anode peak current (hereunder referred to simply as the "secondary peak current") which was the second appearance of anode peak current on each of the electric polarization waveforms shown in FIG. 3. As one can see, the graph of FIG. 4 is in good agreement with the graph of FIG. 1(b) which plots the size of carbides against the specimen type. As mentioned, the same tendency is observed regardless of whether debrittlement is performed or not (namely, irrespective of the degree by which impurities are segregated at grain boundaries) and, hence, one can safely conclude that the secondary peak current is related to the size of carbides, namely, the amount of carbide precipitation and the drop in hardness.

We then conducted an experiment to clarify the phenomenon that occurred in the specimens at the potential for the appearance of the second peak current. To this end, we prepared two kinds of samples for each specimen: one was an as-polished sample yet to be measured and the other was a sample on which the potential sweep was interrupted at the potential value swept just after the appearance of the second peak current following the development of the primary anode peak current. The surface state of these samples was compared by examination of reflected electron images (compositional images) from a scanning electron microscope.

Figure 5A:
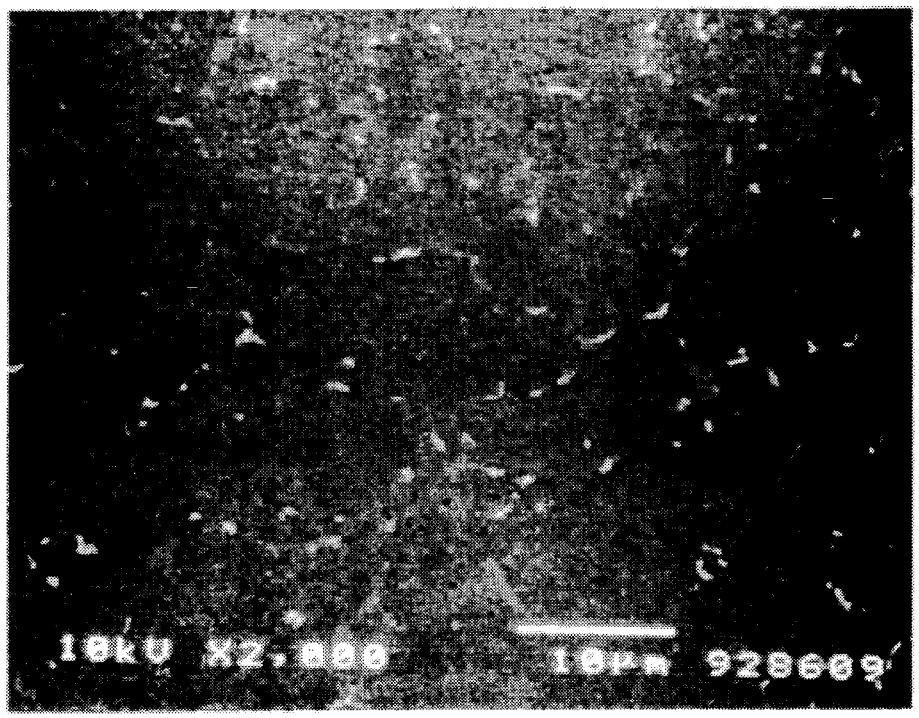
FIGS. 5(a) and 5(b) are a pair of electron micrographs showing the metallurgical structures of two samples of a specimen, FIG. 5(a) showing an as-polished sample, and FIG. 5(b) showing a sample on which the potential sweep was interrupted just after the appearance of the secondary anode peak current.
Figure 5B:
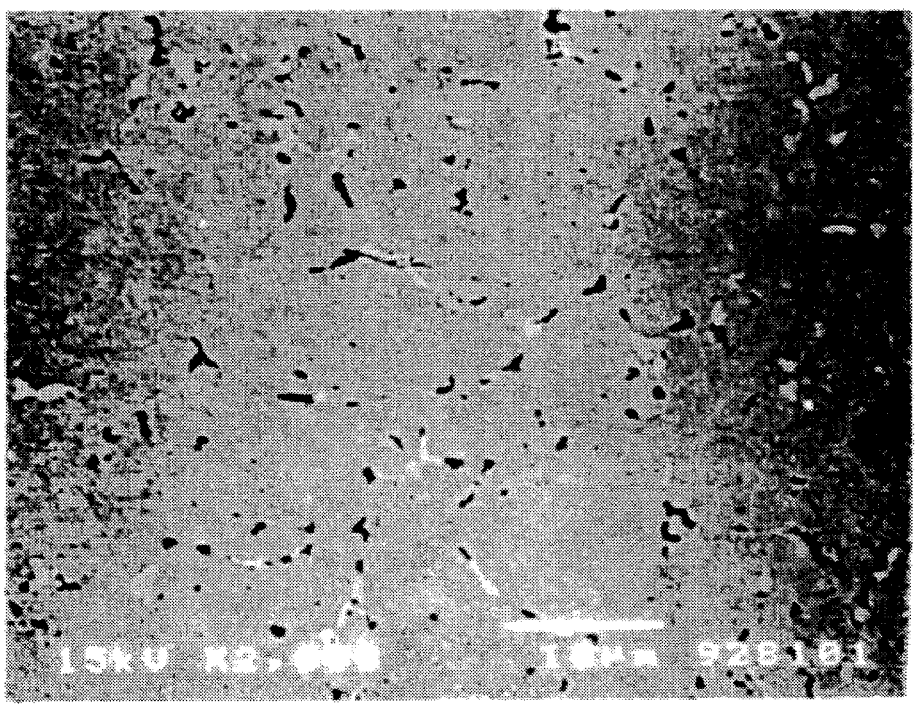

FIGS. 5(a) and 5(b) are a pair of scanning electron micrographs showing the results of examination of the surfaces of the two samples; one (FIG. 5(a)) being the as-polished sample yet to be subjected to the polarization test and the other (FIG. 5(b)) being the sample on which the potential sweep was interrupted (at 400 mV) right after the appearance of the secondary peak current. The position to be examined was the same for both samples. Obviously, the sample examined after the development of the secondary peak current has a clear sign for the disappearance of white spots that are coarse carbide particles formed at grain boundaries. The white carbide spots indicate the presence of elements of high atomic weight.

Figure 6:
FIG. 6 is an electron micrograph showing the metallurgical structure of a sample on which the potential sweep was interrupted after the appearance of the primary anode peak current but before the appearance of the secondary anode peak current.

FIG. 6 is a scanning electron micrograph of a sample that was prepared by interrupting the potential sweep after the development of the primary peak current but before the development of the secondary peak current and which was examined on the surface under the same conditions as adopted for taking photos of FIGS. 5(a) and 5(b). Obviously, white carbide spots are found in FIG. 6.

Samples were also taken from the debrittled specimens and carbide particles were extracted into replicas, which were subjected to carbide identification by an analytical electron microscope; the coarse carbide particles were found to be $M(Fe, Cr)_{23}C_6$ and Mo-rich $M_6C$, with the distribution of fine $M(Fe, Cr)_7C_3$, $Mo_2C$ and $VC$ being observed within crystal grains.

In view of the position and shape of the sign for the disappearance of carbides, as well as the compositional images of the respective samples, the white carbide particles formed by coarse aggregation at grain boundaries were found to be a Mo-rich carbide with the structure identified as $M_6C$.

Figure 7A:
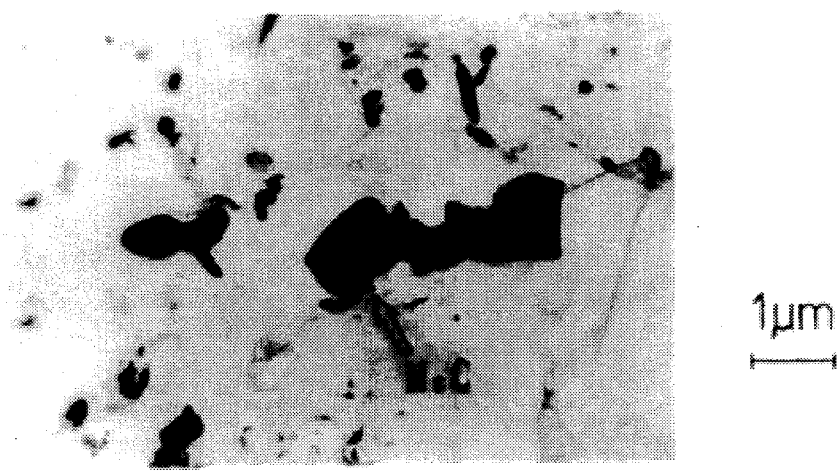
FIGS. 7(a) and 7(b) show the results of analysis for carbides, FIG. 7(a) being an electronmicrograph showing $M_6C$ carbide in the metal matrix, and FIG. 7(b) being a compositional spectrum view of the carbide.
Figure 7B:
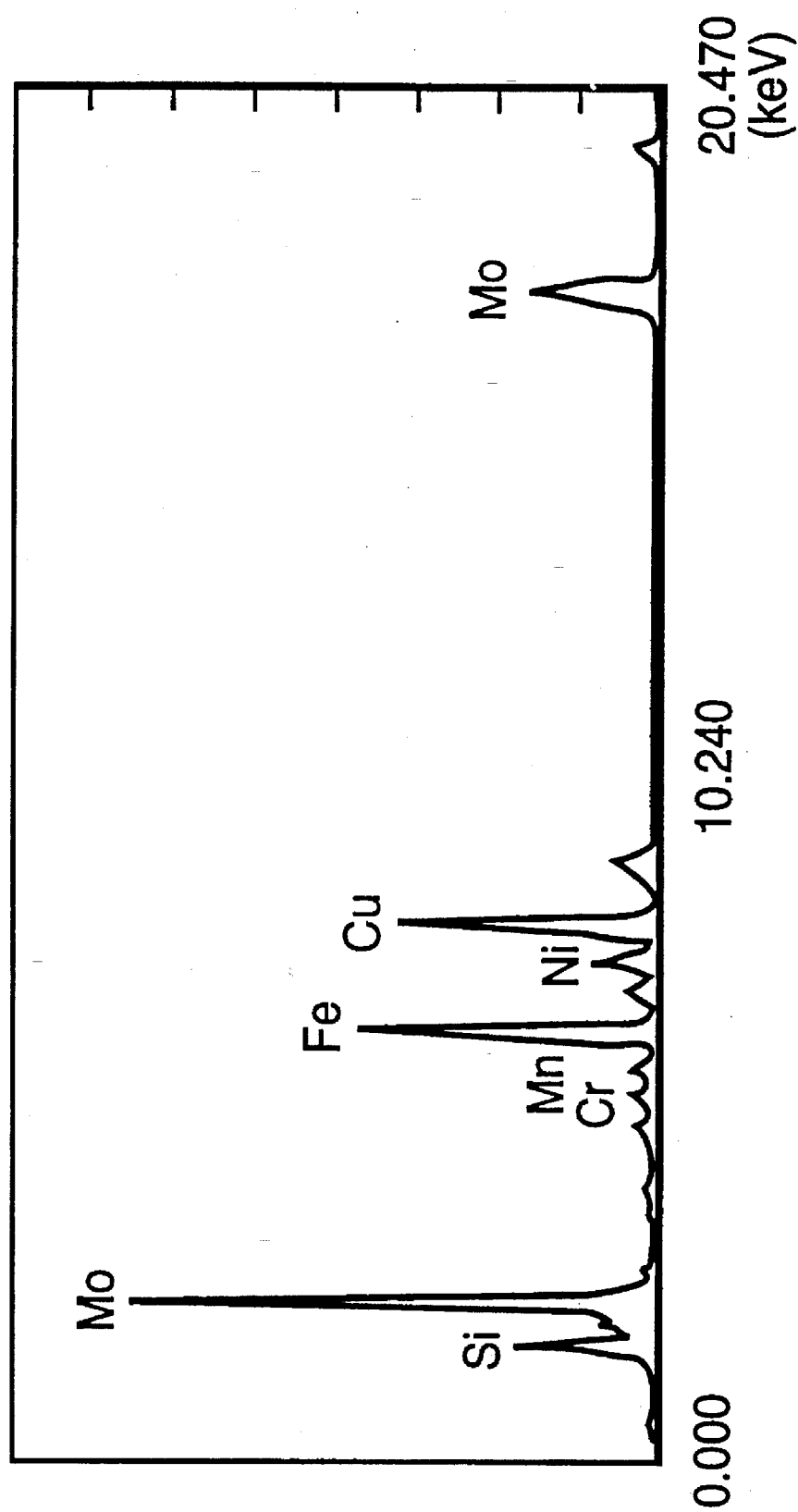
Figure 8:
FIG. 8 is an electron diffraction photograph showing the crystallographic structure of the carbide.

For further identification of the carbide, its component and crystallographic structure were examined under an electron microscope. The results of analysis on the $M_6C$ carbide are shown in FIGS. 7(a) and 7(b); FIG. 7(a) is an electron micrograph showing the $M_6C$ carbide in the metal matrix of the sample and FIG. 7(b) is a compositional spectrum view of the carbide. The Cu component in FIG. 7(b) originates from the copper in the material of the mesh used to extract the carbide; obviously, the Mo-rich carbide contains Mo and Fe as main elements. FIG. 8 is an electron diffraction view showing the crystallographic structure of the carbide, with the result of analysis being shown in Table 2 below.

TABLE 2

| | Results of measurement | $M^6C$ FCC a = 11.082 Å | |
|---|---|---|---|
| No. | Face spacing D (found) (Å) | Face spacing d (calculated) (Å) | hkl |
| 1 | 6.465 | | |
| 2 | 3.319 | 6.398 | 111 |
| 3 | 3.183 | 3.199 | 222 |
| 4 | 3.214 | | |
| 5 | 2.549 | 2.542 | 231 |
| 6 | 2.568 | | |
| 7 | 2.483 | 2.478 | 420 |
| 8 | 2.482 | | |
| 9 | 2.130 | 2.133 | 511 |
| 10 | 2.121 | | |
| 11 | 2.281 | 2.262 | 422 |
| 12 | 2.278 | | |

FIG. 8 and Table 2 show that the Mo-rich carbide is of the $M_6C$ type which has a face-centered cubic structure with a lattice constant a of 11.082Å. In other words, the Mo-rich carbide is $(Mo, Fe)_6C$.

The foregoing discussion leads us to conclude that the secondary peak current is caused chiefly by the dissolution of the Mo-rich carbide $M_6C$. It is generally known that the precipitation of carbides at elevated temperatures is accelerated by the action of stress and this can be used as a technique for evaluating "creep damage", or the progress of material degradation that occurs not merely as the result of time-dependent change at high temperatures but also under the action of an applied stress.

The coarsening of the $M_6C$ carbide particles induces the formation of voids at grain boundaries; this also reduces the content of Mo which contributes to solid solution strengthening while promoting the recovery of dislocations around carbide particles that contribute to the strength. In view of these facts, the coarsening of the $M_6C$ carbide particles into coarse particles is closely related to the softening in hardness and the method of the present invention for detecting the $M_6C$ carbide, which enables the detection of material degradation even if it is of a comparatively slight degree, provides a powerful tool for evaluating the progress of that material degradation. The method of the present invention has a further advantage in that unlike the creep void method, it enables the $M_6C$ carbide to be detected by on-the-spot diagnosis of actual models; therefore, the method of the present invention provides a very useful technique for simple detection on actual models.

The method of the present invention for detecting carbides in alloy steels by electrochemical polarization has been described on the foregoing pages with particular reference to the case where the alloy steel is a CrMoV steel used as the structural material of steam turbines; it should, however, be noted that the concept of the present invention is also applicable to other steel species for detecting the presence and amount of carbides precipitated in the steels.

The CrMoV steel which is an alloy steel will experience creep damage if it is used under a high-temperature and stress-applied condition. Conventionally, this creep damage has been detected in a nondestructive manner by the hardness method or the creep void method but these methods have suffered from various problems in practical applications. The method for detecting carbides in accordance with the present invention has been accomplished in order to solve those problems and it comprises placing a specimen of alloy steel of interest in contact with an electrolyte (saturated picric acid solution) in a polarization measuring cell, impressing a potential between the specimen and a counter electrode in the cell, and sweeping the potential to produce the waveform of electric polarization. This method is characterized by the finding of the fact that the "secondary peak current", or the second appearance of anode peak current on the polarization waveform, is closely related to the precipitation of the Mo-rich carbide $M_6C$ on the surface of the specimen. Since the method of the present invention is adapted for detecting the amount of precipitation of the $M_6C$ carbide, the degree of material deterioration that can be detected by this method is smaller than the degree that can be detected by the conventional creep void method. Even if the part of the machine to be checked has a distribution of initial hardness values, the method insures that the progress of material deterioration can be evaluated in a simple manner without being influenced by that distribution. As a further advantage, the method is applicable to actual models of CrMoV steel made machines for detecting the $M_6C$ carbide on the site of their installation and, hence, the remaining life of the machines can be diagnosed with high operational efficiency and detection precision.

What is claimed is:

1. A method of detecting a carbide in an alloy steel by electrochemical polarization, comprising the steps of:

placing a specimen of said alloy steel in contact with an electrolyte;

sweeping a potential between said specimen and said electrolyte to produce an anode current polarization waveform; and detecting precipitation of a carbide in said specimen and an amount of said carbide on the basis of a secondary anode peak current in said waveform.

2. A method according to claim 1, wherein a saturated picric acid solution is used as said electrolyte.

3. A method according to claim 2, wherein said alloy steel is a CrMoV steel.

4. A method according to claim 3, wherein said carbide is Mo-rich $M_6C$.

5. A method according to claim 2, wherein said carbide is Mo-rich $M_6C$.

6. A method according to claim 1, wherein said alloy steel is a CrMoV steel.

7. A method according to claim 6, wherein said carbide is Mo-rich $M_6C$.

8. A method according to claim 1, wherein said carbide is Mo-rich $M_6C$.

* * * * *